US009845504B2

(12) United States Patent
Juliá Cano et al.

(10) Patent No.: US 9,845,504 B2
(45) Date of Patent: Dec. 19, 2017

(54) METHOD FOR TREATING RHEUMATOID ARTHRITIS WITH AGENTS THAT RECOGNIZE THE B-LYMPHOCYTE CD20 MEMBRANE RECEPTOR

(75) Inventors: Antonio Juliá Cano, Barcelona (ES); Sara Marsal Barril, Barcelona (ES)

(73) Assignee: Fundació Institut de Recerca de L'Hospital Universitari Vall D'Hebron, Barcelona (ES)

( * ) Notice: Subject to any disclaimer, the term of this patent is extended or adjusted under 35 U.S.C. 154(b) by 380 days.

(21) Appl. No.: 13/380,665

(22) PCT Filed: Jun. 9, 2010

(86) PCT No.: PCT/ES2010/070389
§ 371 (c)(1), (2), (4) Date: May 17, 2012

(87) PCT Pub. No.: WO2010/149810
PCT Pub. Date: Dec. 29, 2010

(65) Prior Publication Data
US 2012/0225790 A1    Sep. 6, 2012

(30) Foreign Application Priority Data
Jul. 9, 2010 (ES) .................... 200930349

(51) Int. Cl.
*C12Q 1/68* (2006.01)

(52) U.S. Cl.
CPC ..... *C12Q 1/6883* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2009/0004189 A1    1/2009  Behrens et al.
2009/0204489 A1*   8/2009  Behrens et al. ............. 705/14

OTHER PUBLICATIONS

Raterman et al. (2012) The interferon type I signature towards prediction of non-response to rituximab in rheumatoid arthritis patients. Arthritis Research & Therapy, 15(R95):pp. 1-10.*
Ionnidis, J. (2005) Microarrays and molecular research: noise discovery? Lancet, 365:454-455.*
Michiels et al. (2005) Prediction of cancer outcome with microarrays: a multiple random validation strategy. Lancet, 365:488-492.*
Chuaqui et al. (2002) Post-analysis follow-up and validation of microarray experiments. Nature Genetics Supplement, 32:509-514.*
GSE37107 Probe set excerpt, obtained from <http://www.ncbi.nlm.nih.gov/geo/geo2r/?acc=GSE37107> on Jul. 7, 2014, 1 page.*

Szodoray et al. (2006) A genome-scale assessment of peripheral blood B-cell molecular homeostasis in patients with rheumatoid arthritis. Rheumatology, 45:1466-1476.*
Sekiguchi et al. (2008) Messenger ribonucleic acid expression profile in peripheral blood cells from RA patients following treatment with an anti-TNFa monoclonal antibody, infliximab. Rheumatology, 47:780-788.*
Bleicher et al. (2003) Hit and Lead Generation: Beyond High-Throughput Screening. Nature Reviews Drug Discovery, 2:369-378.*
Julia, Antonio, et al.; "Identification of candidate genes for rituximab response in rheumatoid arthritis patients by microarray expression profiling in blood cells," Pharmacogenomics, 2009, pp. 1297-1308, vol. 10.
Toonen, E J M, et al.; "Gene expression profiling in rheumatoid arthritis: current concepts and future directions," Ann Rheum Dis, 2008, pp. 1663-1669, vol. 67.
Lequerre, Thierry, et al.; "Gene profiling in white blood cells predicts infliximab responsiveness in rheumatoid arthritis," Arthritis Research & Therapy, 2006, pp. 1-11, vol. 8.
Sekiguchi, N., et al.; "Messenger ribonucleic acid expression profile in peripheral blood cells from RA patients following treatment with an anti-TNF-alpha monoclonal antibody, infliximab," Rheumatology, 2008, pp. 780-788, vol. 47.
Koczan, Dirk, et al.; "Molecular discrimination of responders and nonresponders to anti-TNF-alpha therapy in rheumatoid arthritis by etanercept," Arthritis Research & Therapy, 2008, pp. 1-10, vol. 10.
Edwards, Jonathn C.W., et al.; "Efficacy of B-Cell-Targeted Therapy with Rituximab in Patients with Rheumatoid Arthritis," The New England Journal of Medicine, 2004, pp. 2572-2581, vol. 350.
Dass, Shouvik, et al.; "Highly Sensitive B Cell Analysis Predicts Response to Rituximab Therapy in Rheumatoid Arthritis," Arthritis & Rheumatism, 2008, pp. 2993-2999, vol. 58.
Teng, Y. K. Onno, et al.; "Immunohistochemical Analysis as a Means to Predict Responsiveness to Rituximab Treatment," Arthritis & Rheumatism, 2007, pp. 3909-3918, vol. 56.
Cohen, Stanley B.; "Rituximab for Rheumatoid Arthritis Refractory to Anti-Tumor Necrosis Factor Therapy," Arthritis & Rheumatism, 2006, pp. 2793-2806, vol. 54.
Roll, Petra, et al.; "Anti-CD20 Therapy in Patients With Rheumatoid Arthritis," Arthritis & Rheumatism, 2008, pp. 1566-1575, vol. 58.

(Continued)

*Primary Examiner* — Neil P Hammell
(74) *Attorney, Agent, or Firm* — Kilpatrick Townsend & Stockton LLP (57) ABSTRACT

An in vitro method for the prognosis or prediction of response in patients with rheumatoid arthritis to treatment with agents recognising the B-lymphocyte CD20 membrane receptor. The method of the invention comprises an assay in a blood sample from these patients and measuring, before starting the treatment, the transcriptional expression level (mRNA) of at least one of the genes selected from the group: ARG1, CPD, TRAF1, C1QA, LRRN3, LRRN3, HLA-DQA1, NLK, TLR4, LOC89944, TOM1L1, BACH, NCALD, EIF2C2, NFIC, PCDHB7, FLJ32770, ARID3A, C14ORF9, CSNK1E, BCAS1, TEAD2, C6orf145 and SNTA1; and the comparison of this expression level to the expression values previously obtained in patients who responded and who did not respond to the treatment.

3 Claims, 3 Drawing Sheets

(56) References Cited

OTHER PUBLICATIONS

International Search Report, dated Sep. 17, 2010.
Liu, Chunyu et al; Genome-Wide Association Scan Identifies Candidate Polymorphisms Associated with Differential Responde to Anti-TNF Treatment in Rhematoid Arthritis; Mol Med 14(9-10)575-581; Sep.-Oct. 2008.
Coulthard, Lydia et al; Genetic variants within the MAP kinase signaling network and anti-TNF treatment response in rheumatoid arthritis patients; Ann Rheum Dis (2011); 70:98-103.
Potter, C., et al; Association of rheumatoid factor and anti-cyclic citrullinated peptide positivity, but not carriage of shared epitope or PTPN22 susceptibility variants, with anti-tumour necrosis factor response in rheumatoid arthritis; Ann Rheum Dis (2009); 68:69-74.
Krintel, Sophine, et al; Investigation of single nucleotide polymorphisms and biological pathways associated with response to TNFα inhibitors in patients with rheumatoid arthritis; Pharmacogenetics and Genomics (2012); vol. 00 No. 00.
Ao, Lu, et al; Identification of reproducible drug-resistance-related dysregulated genes in small-scale cancer cell line experiments; Scientific Reports( 2015); 5:11895; 1-12.
Cui, Xiangqin, et al; Improved statistical tests for differential gene expression by shrinking variance components estimates; Biostatistics (2005) 6, 1, 59-75.
Benucci et al., "Predictive factors of response to rituximab therapy in rheumatoid arthritis: What do we know today?" Autoimmunity Reviews, Oct. 2010, vol. 9(12), pp. 801-803.
Thurlings et al., "The relationship between the type I interferon signature and the response to rituximab in rheumatoid arthritis," Annals of the Rheumatic Diseases, Mar. 2010, vol. 69, No. Supp. 2, pp. A14-A15.
Vallerskog et al., "Differential effects on BAFF and APRIL levels in rituximab-treated patients with systemic lupus erythematosus and rheumatoid arthritis," Arthritis Research and Therapy, Nov. 2006, vol. 8(6), pp. R167.

\* cited by examiner

METHOD FOR TREATING RHEUMATOID ARTHRITIS WITH AGENTS THAT RECOGNIZE THE B-LYMPHOCYTE CD20 MEMBRANE RECEPTOR

CROSS-REFERENCE TO RELATED APPLICATIONS

This application is filed under the provisions of 35 U.S.C. §371 and claims the priority of International Patent Application No. PCT/ES2010/070389 filed on 9 Jun. 2010 entitled "In Vitro Method for the Prognosis or Prediction of the Response in Patients with Rheumatoid Arthritis Treated with Agents that Recognize the CD20 Membrane Receptor in B Lymphocytes" in the name of Antonio JULIÁ CANO, et al., which claims priority to Spanish Patent Application No. P200930349 filed on 24 June 2009, both of which are hereby incorporated by reference herein in their entirety.

FIELD OF THE INVENTION

This invention relates to an in vitro method (hereafter method of invention) for the prognosis or prediction of response to treatment with agents recognising the B-lymphocyte CD20 membrane receptor, e.g., rituximab, in patients with rheumatoid arthritis (RA). This invention can therefore be considered within the field of personalised medicine, rheumatology or human genetics as a field that studies genetic disorders.

STATE OF THE PRIOR ART

RA is one of the most common autoimmune diseases worldwide (world prevalence ~1%). RA leads to chronic inflammation of synovial joints and to the development of progressive pain in the joints that can lead to marked functional disability. In addition, RA is a highly heterogeneous, complex disease in all respects, including both its clinical symptoms and the variability in its response to the different therapies.

As a result of the intense research conducted in recent years, several treatments have been identified for the control of RA. Rituximab is a monoclonal antibody that recognises the B-lymphocyte-specific CD20 membrane receptor. Rituximab binding to CD20 causes a transient depletion of B lymphocytes. In principle, the drug was designed for the treatment of B-cell non-Hodgkin lymphoma. It has been recently shown that it is also an effective treatment for controlling RA [Edwards, J. C. et al. *Efficacy of B-cell-targeted therapy with rituximab in patients with rheumatoid arthritis.* N Engl J Med 350, 2572-81 (2004)].

However, there is a percentage of patients who do not respond to treatment with agents that recognise the B-lymphocyte CD20 membrane receptor and must be redirected to alternative therapies. Therefore, methods for the prognosis or prediction of patients who may benefit from this treatment and that may differentiate them from patients who do not respond to this treatment that will be directed to alternative therapies are a growing need in the challenge of personalised medicine.

The article [Dass, S. et al. *Highly sensitive B cell analysis predicts response rituximab therapy in rheumatoid arthritis.* Arthritis Rheum 58, 2993-9 (2008)] discloses the association between B lymphocyte depletion levels and clinical response after several weeks. In particular, response to rituximab is worse in individuals with incomplete depletion. The association is statistically significant, but not very strong (P=0.01). In addition, the prediction in this study is performed after receiving the treatment.

Document [Teng, Y. K. et al, *Immunohistochemical analysis as a means to predict responsiveness to rituximab treatment.* Arthritis Rheum 56, 3909-18 (2007)] discloses that patients with high CD79a+B lymphocyte infiltration in the synovial membrane show positive serum tests to anti-cyclic citrullinated peptides (anti-CCPs). The problem with this method is that it only allows for predicting a subgroup of patients and also requires obtaining a synovial biopsy. As compared to blood sampling, the extraction of synovial biopsies is a highly invasive method for the patients and not very practical (few clinical centres have trained personnel and the technology to perform it).

Article [Cohen, S. B. et al. *Rituximab for rheumatoid arthritis refractory to anti-tumor necrosis factor therapy: Results of a multicenter, randomized, double-blind, placebo-controlled, phase trial III trial evaluating primary efficacy and safety at twenty-four weeks.* Arthritis Rheum 54, 2793-806 (2006)] discloses one of the first studies evaluating the efficacy and safety of rituximab in RA. They report a minor and not very significant association between response and rheumatoid factor.

In [Roll, P., Dorner, T. & Tony, H. P. *Anti-CD20 therapy in patients with rheumatoid arthritis: predictors of response and B cell subset regeneration after repeated treatment.* Arthritis Rheum 58, 1566-75 (2008)], an analysis is performed by flow cytometry but, as in Dass et al., weak evocations of lymphocyte subgroups are found with post-treatment clinical response.

None of the documents found in the state of the art describe the genes, the expression of which we analyse to this invention, in order to predict treatment response with agents recognising the B-lymphocyte CD20 membrane receptor, as for instance rituximab, in patients with RA. Therefore, no evidence has been found in thee state of the art regarding the use of the genes mentioned in this invention, and as explained in the description, these have been specifically selected by a comprehensive screening process from among thousands of genes.

Therefore, this invention solves the problems set out in the state of the art providing a method for the prognosis or prediction of patients that can benefit from treatment with agents that recognise the B-lymphocyte CD20 membrane receptor and their differentiation from patients who do not respond to this treatment, who will be directed to alternative therapies.

DESCRIPTION OF THE INVENTION

Brief Description of the Invention

This invention relates to an in vitro method for the prognosis or prediction of response to treatment with agents that recognise the B-lymphocyte CD20 membrane receptor in patients with RA, comprising an assay in a blood sample from these patients and measuring, before starting the treatment, the transcriptional expression level (mRNA) of at least one of the genes selected from Tables 1 to 3, in particular of the group: ARG1, CPD, TRAF1, C1QA, LRRN3, HLA-DQA1, NLK, TLR4, LOC89944, TOM1L1, BACH, NCALD, EIF2C2, NF1C, PCDHB7, FLJ32770, ARID3A, C14ORF9, CSNK1E, BCAS1, TEAD2, C6orf145 and SNTA1; and the comparison of this expression level to the expression values previously obtained in patients who were shown to be responders or non-responders.

In a preferred embodiment of the invention this prognosis is obtained through the expression value resulting from the ARG1/TRAF1 ratio in whole blood. In non-responders responders ARG1 expression is higher than TRAF1 (positive ratio) and in all responders it is the opposite (negative ratio). In addition, this high ARG1 expression is clearly associated with lack of response and the high expression of TRAF1 is predictive of a favourable clinical response to rituximab.

As shown in Tables 1 to 3, it must be considered that, among the particularly preferred genes, the genes that tick over-expressed genes in responders or under-expressed in non-responders before starting treatment are:
TRAF1, LRRN3 and NLK in whole blood.
TLR4, TOM1L1, PCDHB7 and FLJ32770 in CD4+T cells.
C14ORF9, CSNK1E, BCAS1, TEAD2, C6orf145 and SNTA1 in B cells.

In addition, of the particularly preferred genes, the genes that are under-expressed in responders or over-expressed in non-responders before starting treatments are:
ARG1, CPD, C1QA, and HLA-DQA1 in whole blood.
LOC89944, BACH, NCALD, E1F2C2 and NF1C in CD4+T cells.
ARID3A in B cells.

Therefore, the technical problem solved in this invention relates to an in vitro method for the prognosis or prediction of treatment response with agents recognising the B-lymphocyte CD20 membrane receptor (for instance, rituximab) in patients with RA, from blood cells taken from whole blood samples from these patients (comprising 100 % of the cell populations present and not only those of PBMCs cells), that is simple (based on the analysis of a small number of genes) and minimally invasive for the patient (not requiring the extraction of biopsies). In addition, this invention analysed the gene expression pattern in blood cell subpopulations such as CD4+T cells and B cells, finding a number of genes with a statistically significant association between gene expression and the response of RA patients to treatment with rituximab.

It must be highlighted that each of the genes studied in this invention (included in Tables 1 to 3) has in itself predictive potential. Therefore, in the method of the invention any of the genes comprised in Tables 1 to 3 could be used, if there is sufficient evidence of effectiveness, particularly those selected from the group: ARG1, CPD, TRAF1, C1QA, LRRN3, HLA-DQA1, NLK, TLR4, LOC89944, TOM1L1, BACH, NCALD, E1F2C2, NFIC, PCDHB7, FLJ32770, ARID3A, C14ORF9, CSNK1E, BCAS1, TEAD2, C6orf145 and SNTA1, as well as any sub-combination thereof with a number of genes ≥2, or the entire set of genes.

In addition, this invention isolates and analyses mRNA from whole blood without any previous fractionation. The expression profile therefore includes all blood cell populations. This becomes important when we consider that each cell type or population may be associated with different gene expression profiles.

The type of sample taken in a preferred embodiment of this invention (whole blood) makes the method minimally invasive for the patient, since it does not require the extraction of synovial biopsy samples, and can be applied to all patients with RA. In contrast to the synovial sample, the blood sample can be obtained in any clinical centre with very low risk for the patient. In particular, the genes identified using the PaxGene method (see example 2) for preserving RNA are those which allow for faster processing, since they do not require performing any cell separation. However the genes identified in CD4+ and B lymphocytes require a more laborious technical procedure.

The prediction of treatment response in patients with RA is useful in two main ways:
1. Prediction of patients not responding to treatment with agents recognising the B-lymphocyte CD20 membrane receptor: the patient can thus be directed to alternative treatments without needing to apply therapy with agents recognising the B-lymphocyte CD20 membrane receptor as a first treatment. Some of the potential side effects due to treatment with agents recognising the B-lymphocyte CD20 membrane receptor are mentioned in the reference: [*Long term treatment of rheumatoid arthritis with rituximab*. Autoimmunity Reviews. Volume 8, Issue 7, June 2009, Pages 591-594 Roberto Caporali, Maria Caprioli, Francesca Bobbio-Pallavicini, Serena Bugatti and Carlomaurizio Montecucco]
2. Prediction of responders to treatment with agents recognising the B-lymphocyte CD20 membrane receptor: this tool is very useful to start early treatment, since in the particular case of RA it has been shown that treatment in early stages of the disease can be very effective to prevent the progression of joint erosions.

DESCRIPTION OF THE DRAWINGS

FIG. 1. This figure shows the hierarchical analysis of RelDAS28 improvement index measurements (see example 1) in patients treated with rituximab. Two different groups of patients were clearly identified. Based on these results, the patients were classified as responders (n=4, upper cluster) or non-responders to treatment with rituximab (n=5, lower cluster). The height (h) of the dendrogram corresponds to the difference estimated between the individuals, in this case using the Euclidean distance. In this regard, the largest differences (more differentiated clusters) will be the first that appear in the tree and the smallest to those of the last branches. The acronyms R1, R2, R3 and R4 mean, respectively: Responder 1, Responder 2, Responder 3 and Responder 4. The acronyms NR1, NR2, NR3, NR4 and NR5 mean, respectively: Non-responder 1, Non-responder 2, Non-responder 3, Non-responder 4 and Non-responder 5.

DETAILED DESCRIPTION OF THE INVENTION

This invention evaluated the RNA profiles in three different blood cell populations (whole blood, CD4+ cells and lymphocytes) in order to identify genes associated with the response of RA patients to treatment with agents that recognise the B-lymphocyte CD20 membrane receptor. As a result of this evaluation, markers were identified that were able to predict the response of RA patients to treatment with agents recognising, the B-lymphocyte CD20 membrane receptor prior to starting treatment with these agents.

It was thus shown, for instance, that an increase in the expression of the ARG1 gene in whole blood is significantly associated with a worse outcome in therapy with agents recognising the B-lymphocyte CD20 membrane receptor. It has recently been discovered that the ARG1 gene is a significant modulator of inflammatory response by reducing the extracellular availability of arginine and therefore the substrate for the production of pro-inflammatory nitric oxide. Paradoxically, the second gene most commonly associated with treatment response in whole blood, which is also over-expressed in patients not responding to treatment with rituximab, is the CPD coding for carboxypeptidase D. Carboxypeptidase D is an exopeptidase that isolates protein arginine residues increasing the availability of free arginine for the production of nitric oxide. The synthesis of nitric oxide from arginine produces citruline, the antigen of anti-CCP antibodies. These findings suggest that this mechanism of action is relevant in RA. During whole blood analysis, it was also evidenced that over-expression of the TRAF1 gene is associated with a positive response to rituximab in patients with RA.

Also, an increase was identified in the expression of the gene TLR4 in CD4+T cells in patients responding to treatment with rituximab.

ARID3A codes for a specific transcription factor in B cells that increases transcription of the heavy chain of immunoglobulins. This invention evidenced that this gene is over-expressed in patients with RA not responding to rituximab prior to starting treatment.

These findings allowed designing an in vitro method for the prognosis or prediction of treatment response with agents recognising the B-Lymphocyte CD20 membrane receptor in patients with RA, comprising an assay in a blood sample from these patients and measuring the mRNA levels of the expression of at least one of the genes selected from Tables 1 to 3, in particular of the group: ARG1, CPD, TRAF1, C1QA, LRRN3, HLA-DQA1, NLK, TLR4, LOC89944, TOMIL1, BACH, NCALD, EIF2C2, NFIC, PCDHB7, FLJ32770, ARID3A, C14ORF9, CSNK1E, BCAS1, TEAD2, C6orf145 and SNTA1, and the comparison of this expression level to the expression values previously obtained in patients who were shown to be responders or non-responders. In case the method of the invention is performed based on the expression value resulting of the ARG1/TRAF1 ratio, the prognosis can be performed directly without comparing this value to the values obtained in control individuals.

A group of genes significantly associated with response to treatment with rituximab was identified with patients with RA using a microarray. Statistically significant genes were determined in whole blood. CD+T cells and B cells. The most relevant candidates were also validated by RT-PCR. The subgroups of validated genes are a new group of markers for predicting the response to treatment with rituximab in patients with RA.

EXAMPLES

Example 1. Patient Selection

Patients with RA were initially selected at the Rheumatology Unit of the Hospital Universitario Vall d'Hebron (Barcelona, Spain). All patients had been diagnosed RA following the criteria established by the American College of Rheumatology (ACR). The patients selected for treatment had active RA: DAS28 index (Disease activity score >5.1). The clinical assessment of patients using the DAS28 index was performed every three months of treatment. All procedures conducted are in line with the Declaration of Helsinki. The study was approved by the Ethics Committee of the Hospital Universitario Vall d'Hebron.

Figure 1:
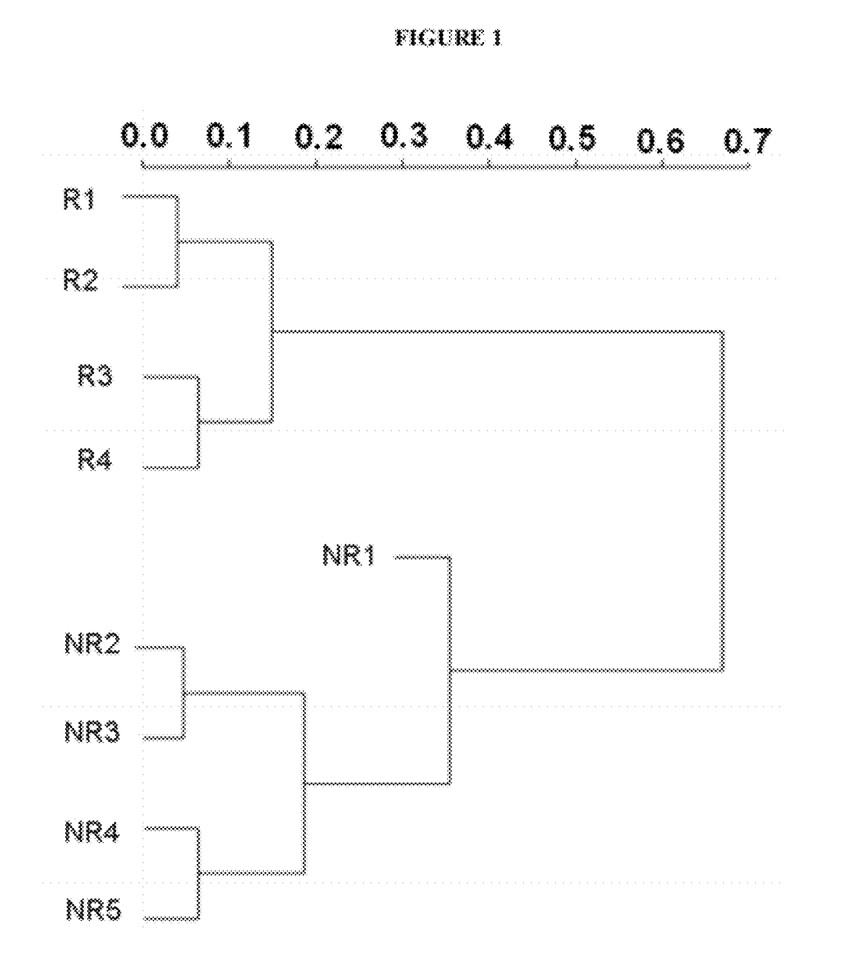

A positive result was obtained in the rheumatoid factor (RF) scrology test in eight of the patients treated with rituximab. In addition, five of the patients were anti-CCP (anti-cyclic cytrullinated peptide) positive. All patients were women in which treatment with anti-TNF agents had failed. After intravenous administration of methyl prednisone at a dose of 100 mg, all patients received an infusion of 1 g of rituximab on Days 1 and 15 of the treatment. The clinical response to rituximab was established at Week 24 using the RelDAS28 index. With this method, the efficacy of a particular treatment is estimated through the improvement in the relative DAS28 index. Subsequently, analytical methods (hierarchical clustering) were applied to identify patient groups with similar responses to treatment with rituximab (FIG. 1).

EXAMPLE 2. Blood Sampling

The blood samples for RNA sampling were taken from the patients during the first day of application of rituximab.

This invention used the "PAXGene" system (PreAnalytix, Switzerland) for immediate preservation of the RNA from whole blood samples. This system uses a RNA-preserving agent contained in the same blood sampling tube and the blood profiles obtained are thus representative of in vivo conditions. All "PAXGene" tubes were stored frozen at −80° C. until the RNA was isolated. The RNA was taken using the "PAXGene" full isolation kit (Qiagen, US). Finally, the quality of the RNA of all samples was assessed using the "BioAnalyzer" gel system (Agilent, USA).

EXAMPLE 3. Analysis by Flow Cytometry

The analysis by flow cytometry was performed on all patients included in the study the same day of blood sampling for the microarray assay. Subpopulations of leukocytes and red blood cells were determined from the whole blood sample. In order to estimate the cell purity level obtained in the lymphocyte selection step, determination by flow cytometry of CD4+T and CD20+B cells was also performed.

EXAMPLE 4. Analysis of Gene Expression

The analysis of gene expression of the entire genome was performed using the Illumina Human-6 v1 Beadchip array system (Illumina). By using the bead-based technology, the microarray used in this invention assessed the expression of 47,000 transcripts The good quality RNAs (ratio 28S/18S>1.8, RNA Integrity Number >9) were subsequently processed using this standard Illumina protocol. After sample labelling and hybridisation, the arrays were read using the lumina BeadArray Reader. The data was taken using the "Illumina BeadStudio" software. The other steps were performed using the R software and its extension for genomic data analysis in the "Bioconductor" software. At the time of data analysis, an updated version of the IlluminaHuman-6 v2, Beadchip array had appeared. This new version includes a substantial redesign of the wave sequence and, therefore, the microarray assay was limited to the portion of probes considered valid according to the new microarray version. The values of the final expression of the transcripts were transformed into log 2 and standardised using the quantile normalization method (Bolstad Bioinformatics '03). Before performing any statistical analysis, a hierarchical clustering was performed to identify and rule out any possible microarray with outliers.

EXAMPLE 5. Analysis by RT-PCR

Reverse transcription of RNA samples obtained from the three types of cells was performed using the cDNA Archive Kit from Applied Biosystems. Determination by RT-PCR of the whole of candidate genes was performed using predesigned TaqMan assays by Applied Biosystems. The gene expression tests Hs00194639_m1 and Hs00163660_m1 were used for whole blood to measure TRAF1 and ARG1 genes, respectively, and to analyse the correlation with the microarray data using the ratio obtained from the two measurements. Endogenous controls were sought for each candidate lymphocyte from the group of genes showing very low variation in the microarray data.

Example 6 Statistical Analysis

All statistical analyses were performed using the method set out in [R: A Language and Environment for Statistical Computing. In: R Development Core Team; 2006]. The genes expressed differentially among responders to treatment with rituximab and non-responders were measured using the Welch test implemented in the multitest package. Test corrections were performed using the Benjamini and Hochber False Discovery Rate method. The gene ontology analysis was performed using the GOstat analysis tool [Beissbarth T. Speed T P. GOstat: *find statistically overrepresented Gene Ontologies within a group of genes*. Bioinformatics 2004;20(9):1464-5.] Correlations between the microarray and the measurements of gene expression by RT-PCR were calculated using the Pearson correlation coefficient.

RESULTS

Example 7. Patient Classification

The hierarchic analysis of the RelDAS28 measurements of the patients treated with rituximab clearly identified two different patient groups (FIG.1). Based on these results, the patients were classified as responders (n=4, left cluster) or non-responders to treatment with rituximab (n=5, right cluster).

Example 8. Determination of Genes Associated with Response to Rituximab

Seven genes were identified by the analysis of gene expression in the microarray (ARG1, CPD, TRAF1, C1QA, LRRN3, HLA-DQA1 and NLK) that were differentially expressed in whole blood profiles of patients with RA treated with rituximab (P<0.05). The analysis of CD4+T cells and B cell subpopulations identified 33 and 50 differentially expressed genes between responders and non-responders. Tables 1 to 3 show a list of the most significant for each of the three cell types.

Example 9. Analysis of Candidate Genes by RT-PCR

Figure 2:
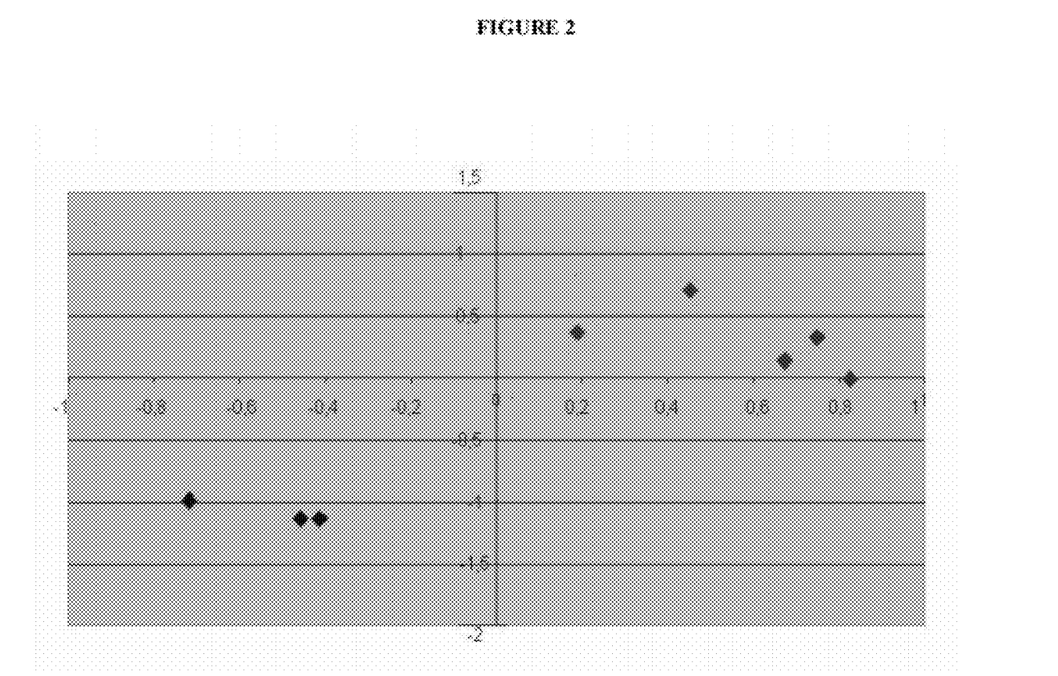
FIG. 2. This figure shows that the ratio of the expression of ARG1 to TRAF1 (ARG1/TRAF1) genes in patients responding to treatment with rituximab (diamonds in the left lower quadrant) and non-responders (diamonds in the right upper quadrant) is consistent with the microarray assay (X axis) and the RT-PCR assay (Y axis). Moreover, both groups of patients are clearly separated.
Figure 3:
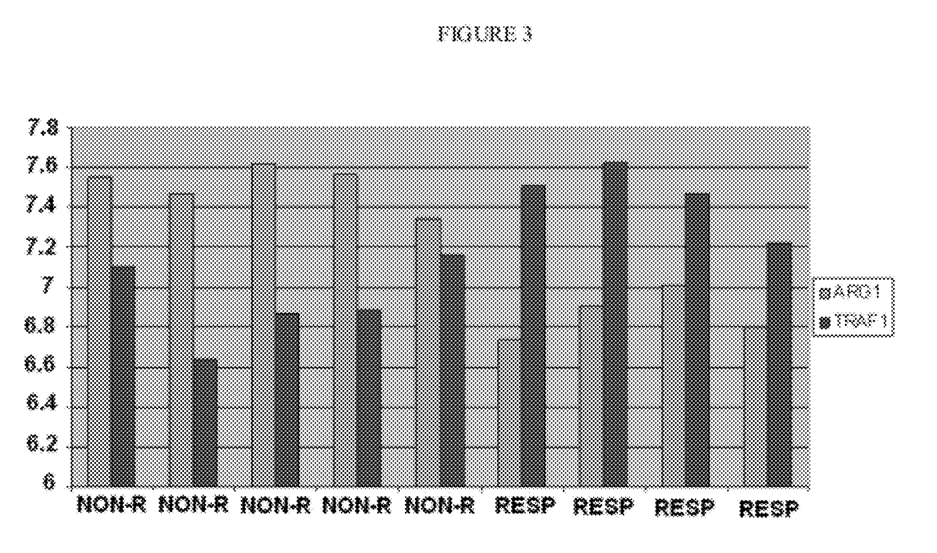
FIG. 3. This figure shows the expression of the ARG1 and TRAF1 genes in whole blood of patients treated with rituximab. It shows clearly that in non-responders ARG1 expression is higher than TRAF1 (positive ratio) and in all responders it is the opposite (negative ratio). In addition, this high ARG1 expression is clearly associated with lack of response and the high expression of TRAF1 is predicative of a favourable clinical response to rituximab.

In whole blood a high correlation was seen between the microarray and the RT-PCR assays (r=0.75). FIG. 2 shows a clear separation between responders and non-responders to treatment with rituximab that is obtained using the microarray values or the RT-PCR of the ARG1 and TRAF1 genes. The validation of the CD4+T cells also showed a high correlation with the determination of TLR4 (r=0.91). In B cells, however, the differential expression seen in the microarray was not replicated (r=0.47).

TABLE 1

List of genes differentially expressed in B cells (B lymphocytes) in patients with RA responding to therapy with rituximab vs non-responders. The bolded genes are those with higher statistical significance.

| Expression level | p (statistical significance) | NCBI access no. | Symbol | Synonym symbols |
| --- | --- | --- | --- | --- |
| −2.12 | 1.88E−49 | NM_005224.1 | ARID3A | DRIL1; BRIGHT; E2FBP1 |
| 2.04 | 1.05E−11 | NM_144568.1 | C14orf9 | MGC26684; DKEZp434M0519 |
| 1.61 | 2.14E−08 | NM_001894.4 | CSNKIE | HCKIE; MGC10398 |
| 1.48 | 1.67E−07 | NM_003657.1 | BCAS1 | AIBC1; NABC1 |
| 1.51 | 3.64E−06 | NM_003598.1 | TEAD2 | ETF; TEF4; TEF-4 |
| 1.48 | 1.98E−05 | NM_183373.2 | C6orf145 | |
| 1.63 | 8.08E−05 | NM_003098.2 | SNTA1 | SNT1; TACIP1; dJ1187J4.5 |
| −1.57 | 0.000235777 | NM_004972.2 | JAk2 | |
| 1.61 | 0.00027208 | NM_012225.1 | NUBP2 | CFD1 |
| 1.83 | 0.000387337 | NM_022489.1 | FLJ22056 | |
| 1.49 | 0.000499237 | NM_138783.1 | LOC115950 | |
| 1.67 | 0.000718414 | NM_006330.2 | LYPLA1 | LPL1; APT-1; LYSOPLA |
| −1.48 | 0.000808462 | NM_002267.2 | KPNA3 | SRP4; IPOA4; hSRP1; SRP1gamma |
| 1.52 | 0.000808462 | NM_032815.2 | FLJ14639 | |
| 1.77 | 0.001108053 | NM_024667.1 | FLJ12750 | |
| −1.64 | 0.001299768 | NM_005248.1 | FGR | SRC2; c-fgr; p55c-fgr |
| 1.52 | 0.001546683 | NM_175870.3 | LOC90925 | |
| 1.47 | 0.002544314 | NM_138447.1 | LOC115509 | |
| −1.66 | 0.00347845 | NM_000402.2 | G6PD | G6PD1 |
| 1.46 | 0.00347845 | NM_012239.3 | SIRT3 | SIR2L3 |
| −1.56 | 0.004199385 | NM_019043.2 | APBB1IP | RIAM; INAG1 |

TABLE 1-continued

List of genes differentially expressed in B cells (B lymphocytes) in patients with RA responding to therapy with rituximab vs non-responders. The bolded genes are those with higher statistical significance.

| Expression level | p (statistical significance) | NCBI access no. | Symbol | Synonym symbols |
|---|---|---|---|---|
| 1.63 | 0.004199385 | NM_013337.1 | TIMM22 | TEX4; TIM22 |
| 1.48 | 0.005042721 | NM_053004.1 | GNB1L | GY2; FKSG1; WDR14; WDVCF; DGCRK3; KIAA1645 |
| 1.59 | 0.005042721 | NM_031420.2 | MRPL9 | L9mt |
| 1.50 | 0.005137737 | NM_003926.5 | MBD3 | |
| −1.42 | 0.006569589 | NM_016575.1 | TU12B1-TY | |
| 1.62 | 0.009179039 | NM_0I6948.1 | PARD6A | PAR-6; TAX40; PAR-6A; TIP-40; PAR6alpha |
| −1.77 | 0.009238875 | NM_013333.2 | EPN1 | |
| −1.85 | 0.011214848 | NM_000700.1 | ANXA1 | ANX1; LPC1 |
| −2.98 | 0.012258881 | NM_000518.4 | HBB | |
| −1.42 | 0.018829774 | NM_005115.3 | MVP | LRP; VAULT1 |
| −1.81 | 0.020051909 | NM_002863.2 | PYGL | |
| 1.41 | 0.020051909 | NM_024734.2 | CLMN | calmin; FLJ12383; KIAA1188 |
| −1.66 | 0.020051909 | NM_006483.1 | DYRK1B | MIRK |
| 1.66 | 0.022202324 | NM_005001.1 | NDUFA7 | B14.5a |
| 1.81 | 0.02446468 | NM_152312.2 | GYLTL1B | FLJ35207 |
| 1.39 | 0.02440468 | NM_153188 | TNPO1 | MIP; TRN; IP02; MIP1; KPNB2 |
| −1.63 | 0.025247943 | NM_002339.1 | LSP1 | WP34; pp52 |
| −1.37 | 0.026585392 | NM_053276.2 | VIT | |
| −1.85 | 0.026726011 | NM_005566.1 | LDHA | LDH1 |
| −1.53 | 0.02724486 | NM_002502.2 | NFKB2 | LYT10; LYT-10 |
| 1.69 | 0.031332618 | NM_033419.3 | CAB2 | PP1498; AGLA546; MGC9753 |
| −1.42 | 0.033641657 | NM_012447.1 | STAG3 | MGC2463 |
| −1.54 | 0.033641657 | NM_138392.1 | LOC92799 | |
| −1.44 | 0.041259852 | NM_198495.1 | FLJ43692 | |
| −1.34 | 0.04281618 | XM 292049.3 | LOC341416 | |
| 1.52 | 0.04281618 | NM_015568.2 | PPP1R16B | TIMAP; ANKRD4; KIAA0823 |
| 1.39 | 0.043017515 | NM_004436.1 | ENSA | |
| 1.51 | 0.046241371 | NM_145012.3 | C10orf9 | CFP1; CBCP1 |
| 1.42 | 0.046826639 | NM_017980.2 | LIMS2 | PINCH-2; FLJ10044 |

TABLE 2

List of genes differentially expressed in CD4+T cells (T-CD4 lymphocytes) in patients with RA responding to therapy with rituximab vs non-responders. The bolded genes are those with higher statistical significance.

| Expression level | p (statistical significance) | NCBI access no. | Symbol | Synonym symbols |
|---|---|---|---|---|
| 1.37 | 5.16E−13 | NM_138557.1 | TLR4 | TOLL; hToll |
| −1.48 | 4.54E−10 | NM_138342.2 | LOC89944 | |
| 1.38 | 5.95E−07 | NM_005486.1 | TOM1LI | SRCASM |
| −1.50 | 1.33E−05 | NM_181866.1 | BACH | ACT; ACH1; LACH1; hBACH; CTE-II; MGC1126 |
| −1.47 | 5.33E−05 | NM_032041.1 | NCALD | |
| −1.68 | 0.000101326 | NM_012154.2 | E1F2C2 | Q10; AG02; MGC3183 |
| −1.69 | 0.000549477 | NM_005597.2 | NF1C | CTF; NF1; CTF5; NF-1; MGC20153 |
| 1.35 | 0.000566469 | NM_018940.2 | PCDHB7 | PCDH-BETA7 |
| 1.34 | 0.000652274 | NM_182525.1 | FLJ32770 | |
| 1.32 | 0.003712105 | NM_004432.1 | ELAVL2 | HUB; HELN1; HEL-N1 |
| 1.99 | 0.003712105 | XM_065237.5 | LOC129439 | |
| −1.64 | 0.003712105 | NM_130783.2 | LOC90139 | TSPAN |
| 1.38 | 0.008059177 | NM_000818.1 | GAD2 | GAD65 |
| 1.40 | 0.008427 | NM_007160.2 | OR2H3 | FAT11; 0LFR2 |
| 1.54 | 0.008427 | NM_005611.2 | RBL2 | Rb2; P130 |
| −1.31 | 0.008427 | NM_031274.2 | TEX13A | |
| 1.31 | 0.010149379 | NM_032854.1 | FLJ14871 | |
| −1.36 | 0.01223528 | NM_021622.2 | PLEKHA1 | TAPP1 |
| 1.48 | 0.019282522 | NM_002227.1 | JAK1 | JAK1A |
| 1.47 | 0.019323333 | NM_000801.2 | FKBP1A | FKBP1; PKC12; PKC12; FKBP12; PPIASE; FKBP-12; FKBP12C |

TABLE 2-continued

List of genes differentially expressed in CD4+T cells (T-CD4 lymphocytes) in patients with RA responding to therapy with rituximab vs non-responders. The bolded genes are those with higher statistical significance.

| Expression level | p (statistical significance) | NCBI access no. | Symbol | Synonym symbols |
|---|---|---|---|---|
| −1.43 | 0.021500376 | NM_022070.3 | ABC1 | FLJ22087 |
| −1.33 | 0.021500376 | NM_032788.1 | ZNF514 | FLJ14457 |
| −1.61 | 0.022435284 | NM_003403.3 | YY1 | DELTA; NF-E1; UCRBP; YIN-YANG-1 |
| 1.41 | 0.02504827 | NM_017585.2 | SLC2A6 | GLUT6; GLUT9; HSA011372 |
| 1.42 | 0.02504827 | NM_174943.2 | FLJ25976 | |
| 1.32 | 0.028705236 | NM_004543.2 | NEB | NEM2 |
| 1.33 | 0.030870305 | NM_198945.1 | ALS2CR17 | |
| −1.32 | 0.030870305 | NM_144490.1 | AKAP11 | PRKA11; AKAP220: FLJ11304; KIAA0629 |
| −1.52 | 0.033230235 | NM_017668.1 | NDE1 | NUDE: NUDE1; FLJ20101 |
| 1.40 | 0.035705721 | NM_001970.3 | EIF5A | EIF-5A; EIF5A1 |
| −1.53 | 0.038879229 | NM_015897.2 | PIASY | MGC35296 |
| −1.48 | 0.03969694 | NM_002168.2 | IDH2 | IDH; IDP; IDHM; ICD-M; mNADP-IDH |
| 1.28 | 0.04545963 | NM_022337.1 | RAB38 | NY-MEL-1 |

TABLE 3

List of genes differentially expressed in whole blood cells in patients with RA responding to therapy with rituximab vs non-responders.

| Expression level | p (statistical significance) | NCBI access no. | Symbol | Synonym symbol |
|---|---|---|---|---|
| −1.56 | 3.06E−17 | NM_000045.2 | ARG1 | |
| −1.52 | 7.72E−07 | NM_001304.3 | CPD | |
| 1.44 | 0.017986457 | NM_005658.2 | TRAF1 | EBI6; MGC: 10353 |
| −1.47 | 0.022919791 | NM_015991.1 | C1QA | |
| 1.56 | 0.022919791 | NM_018334.3 | LRRN3 | NLRR3; NLRR-3; FLJ11129 |
| −2.48 | 0.022919791 | XM_371812.1 | HLA-DQA1 | DQA1; HLA-DQ; CELIAC1; HLA-DQA |
| 1.36 | 0.031396183 | NM_016231.2 | NLK | |

The ARG1, TRAF1, TLR4 and ARID3A genes were analysed by RT-PCR.

All genes mentioned in Tables 1 to 3 are statistically significant, and each can therefore be used effectively in the method of the invention. However, the bolded genes are part of a preferred embodiment of the invention, since these genes showed the highest statistical significance.

As shown in Tables 1 to 3, a group of seven differentially expressed genes was identified in whole blood in patients responding to therapy with rituximab vs non-responders. Also shown are the genes with a higher statistical significance expressed in CD4+T and B cells, differentially expressed in patients responding to therapy with rituximab vs non-responders (P<0.0001, n=9 n=7, respectively).

The invention claimed is:

1. A method for the prognosis and treatment of rheumatoid arthritis in a patient, the method comprising:
   (a) obtaining a blood cell sample from a human patient;
   (b) detecting an expression level of the ARG1 gene and an expression level of the TRAF1 gene in the blood cell sample;
   (c) predicting that the patient will respond to treatment with rituximab when the expression level of the ARG1 gene is lower than the expression level of the TRAF1 gene; and
   (d) administering an effective amount of rituximab to the patient.

2. The method according to claim 1, wherein the expression levels of the ARG1 gene and the TRAF1 gene are detected by quantitation of mRNA levels in the blood cell sample.

3. The method according to claim 1, wherein the expression levels of the ARG1 gene and the TRAF1 gene are detected by:
   reverse transcribing mRNA from the ARG1 gene and the TRAF1 gene;
   generating complementary DNA (cDNA) associated with the ARG1 gene and the TRAF1 gene from the mRNA; and
   amplifying the cDNA associated with the ARG1 gene and the TRAF1 gene to detect the expression levels of the ARG1 gene and the TRAF1 gene.

* * * * *